United States Patent

Popescu

(10) Patent No.: US 7,643,606 B2
(45) Date of Patent: Jan. 5, 2010

(54) X-RAY COMPUTED TOMOGRAPHY APPARATUS WITH LIGHT BEAM-CONTROLLED X-RAY SOURCE

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 12 days.

(21) Appl. No.: 11/674,720

(22) Filed: Feb. 14, 2007

(65) Prior Publication Data

US 2007/0189441 A1      Aug. 16, 2007

(30) Foreign Application Priority Data

Feb. 14, 2006      (DE) ........................ 10 2006 006 840

(51) Int. Cl.
*G01N 23/083*      (2006.01)
(52) U.S. Cl. ............................... 378/10; 378/9; 378/19
(58) Field of Classification Search ...................... 378/9, 378/10, 19
See application file for complete search history.

(56) References Cited

U.S. PATENT DOCUMENTS

| 4,352,021 | A |   | 9/1982  | Boyd et al. |         |
|-----------|---|---|---------|-------------|---------|
| 4,606,061 | A |   | 8/1986  | Ramamurti   |         |
| 5,172,401 | A | * | 12/1992 | Asari et al.   | 378/10 |
| 5,490,193 | A | * | 2/1996  | Kuroda et al.  | 378/10 |
| 5,491,734 | A | * | 2/1996  | Boyd et al.    | 378/10 |
| 6,181,765 | B1 |   | 1/2001  | Sribar et al. |         |
| 6,385,292 | B1 | * | 5/2002 | Dunham et al.  | 378/122 |
| 6,400,791 | B1 | * | 6/2002 | Schwarz        | 378/17 |
| 6,731,716 | B2 |   | 5/2004 | Mihara et al.  |         |
| 6,735,271 | B1 | * | 5/2004 | Rand et al.    | 378/4 |
| 7,023,950 | B1 | * | 4/2006 | Annis          | 378/2 |
| 7,085,350 | B2 | * | 8/2006 | Dunham et al.  | 378/119 |
| 7,085,352 | B2 | * | 8/2006 | Dunham         | 378/122 |
| 7,203,269 | B2 | * | 4/2007 | Huber et al.   | 378/10 |
| 7,233,644 | B1 | * | 6/2007 | Bendahan et al. | 378/57 |
| 7,428,297 | B2 | * | 9/2008 | Eilbert        | 378/134 |
| 2002/0094064 | A1 |   | 7/2002 | Zhou et al.  |         |
| 2006/0002514 | A1 |   | 1/2006 | Dunham       |         |

\* cited by examiner

*Primary Examiner*—Irakli Kiknadze
*Assistant Examiner*—Thomas R Artman
(74) *Attorney, Agent, or Firm*—Schiff Hardin LLP

(57) ABSTRACT

An x-ray computed tomography apparatus has a stationary x-ray detector that at least partially surrounds the examination volume in one plane and a stationary device for generation of x-ray radiation. The device for generation of x-ray radiation is composed of an x-ray source that extends annularly around the examination volume over an angle of at least 180° as well as one or more light scanning units with which an x-ray focus moving along the x-ray source can be generated on the x-ray target by scanning of the x-ray source with a light beam, from which x-ray target an x-ray beam is directed through the examination volume onto respective, momentarily opposite detector elements of the stationary x-ray detector. The computed tomography apparatus has one or more light scanning units are arranged and fashioned outside of a central ring axis of the x-ray source such that only an angle range <360° is respectively scanned with each light scanning unit without crossing the ring axis.

6 Claims, 4 Drawing Sheets

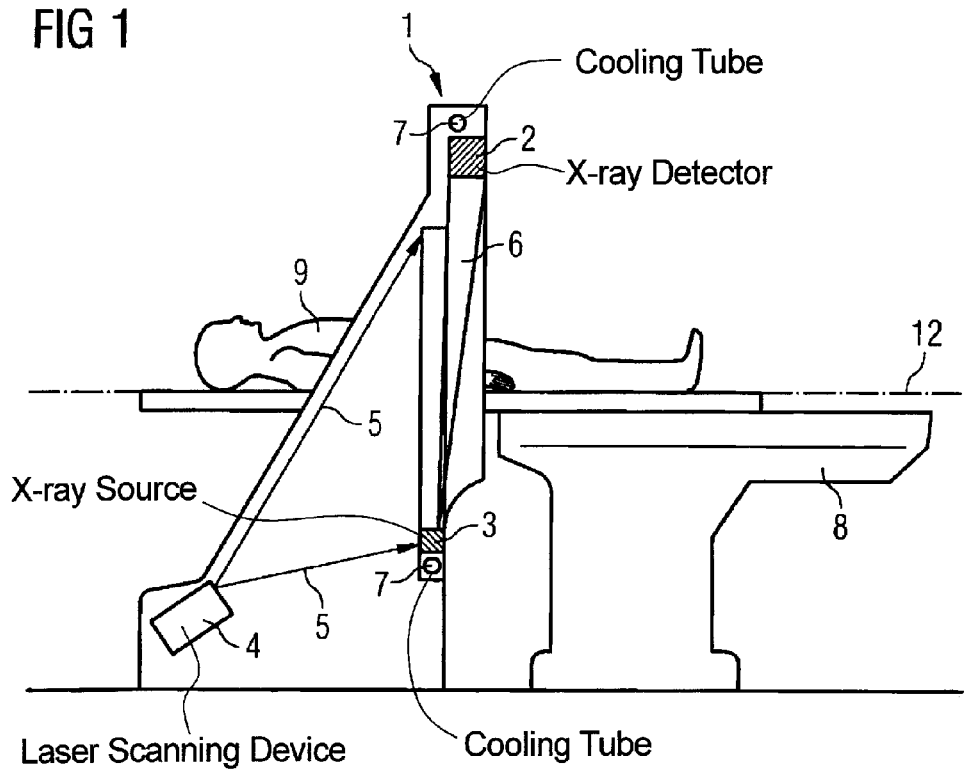
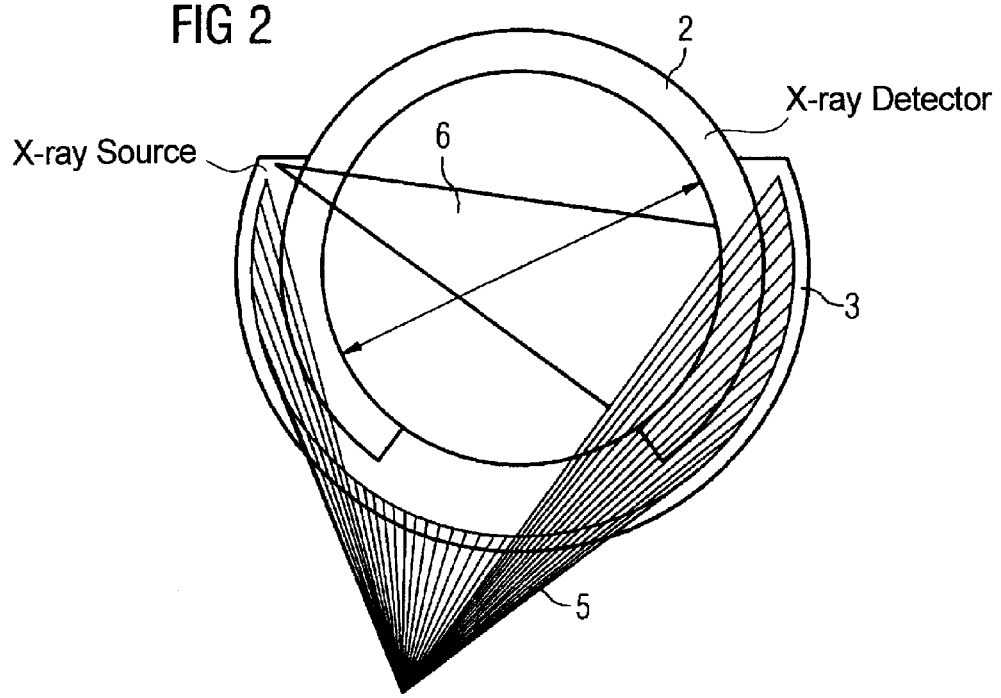

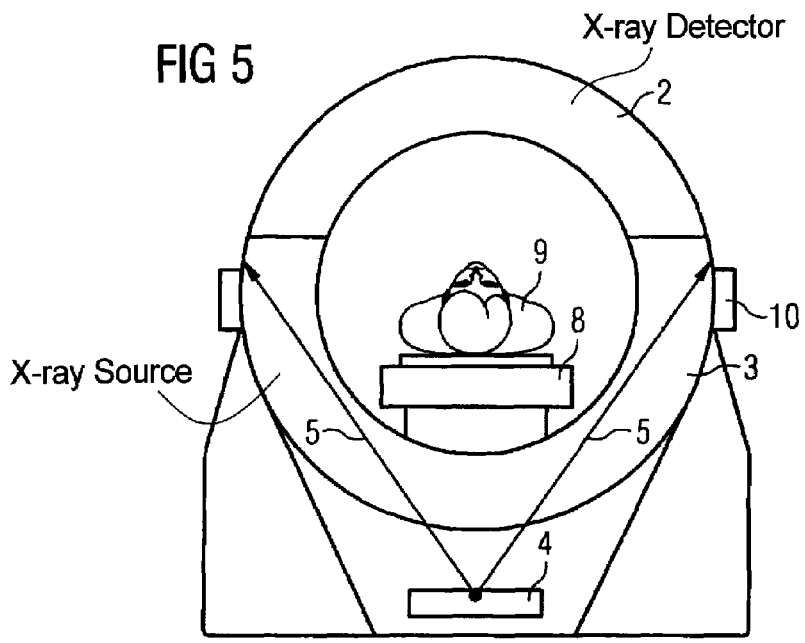
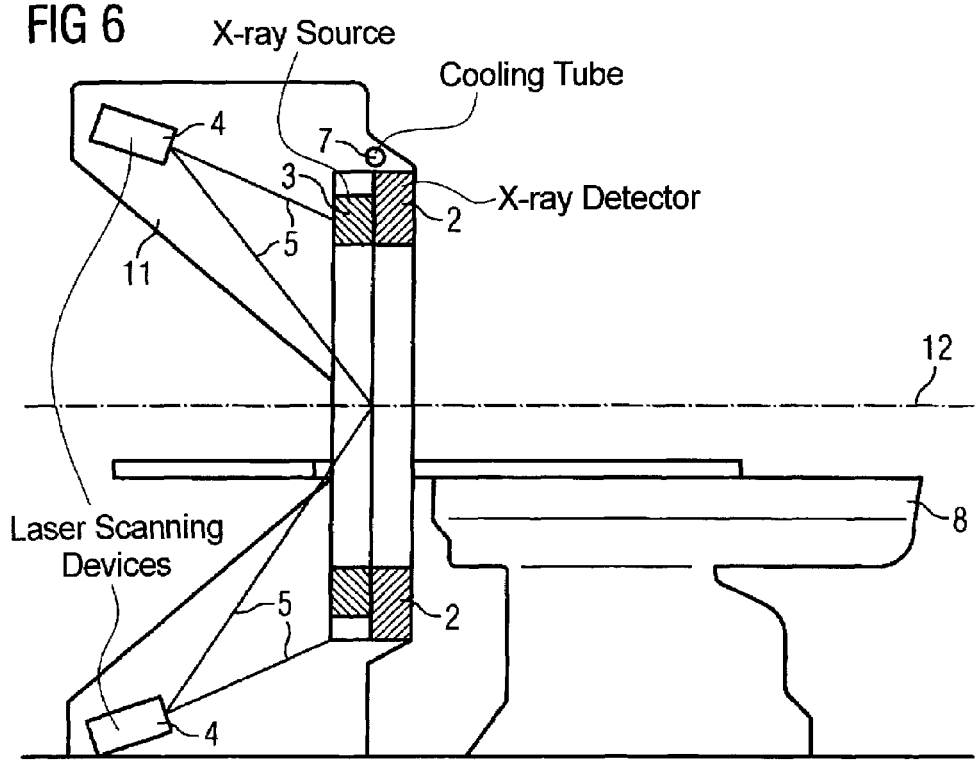

X-RAY COMPUTED TOMOGRAPHY APPARATUS WITH LIGHT BEAM-CONTROLLED X-RAY SOURCE

BACKGROUND OF THE INVENTION

1. Field of the Invention

The present invention concerns an x-ray computed tomography apparatus of the type having a stationary x-ray detector that at least partially encloses an examination volume in one plane; and a stationary device for generation of x-ray radiation, the stationary device including an x-ray source that extends annularly over an angle of at least 180° around the examination volume; and including one or more light scanning units with which an x-ray focus moving along the x-ray source can be generated by scanning of the x-ray source; from which x-ray focus an x-ray beam is directed through the examination volume onto respective, momentarily opposite detector elements of the stationary x-ray detector.

2. Description of the Prior Art

Computed tomography apparatuses are used, for example, in medical imaging in order to acquire images of the inside of the body of a patient. A computed tomography apparatus includes, among other things, a device for generation of x-ray radiation, an x-ray detector and a patient positioning table with which the examination subject can be moved through the examination volume along a system axis (known as the Z-axis) during the examination. The device for generation of x-ray radiation generates an x-ray beam that emanates from an x-ray focus that rotates around the examination volume. In examinations the x-ray beam, expanded in a fan shape in a slice plane of the examination volume (X-Y plane) perpendicular to the system axis, penetrates a slice of the examination subject, for example a body slice of a patient, and strikes the detector elements of the x-ray detector situated opposite the x-ray focus. The angle at which the x-ray beam penetrates the body slice of the subject and, if applicable, the position of the patient positioning table normally varies continuously during the image acquisition with the computed tomography apparatus.

In computed tomography apparatuses of the third generation the rotating x-ray focus is generated by an x-ray tube that, like the x-ray detector, is fastened on a rotary frame (gantry) that is rotatable around the examination volume. The rotation speed of the rotary frame in recent years has been steadily increased in order to achieve faster scan speeds in the image acquisition. For reasons of mechanical stability and safety, however, in computed tomography apparatuses of the third generation a limit has been reached that, due to the masses to be moved and the high acceleration forces resulting therefrom, no longer allows a significant increase of the rotation speed of the rotary frame.

In computed tomography apparatuses of the fourth generation the x-ray detector is arranged as a stationary ring around the examination volume so that only the x-ray tube must still be moved with the rotary frame. Here as well, however, significant forces that limit the rotation speed act on the x-ray tube so a further increase of the rotation speed of the rotary frame is not likely.

To avoid this problem, computed tomography apparatuses of the fifth generation have become known in which both the device for generation of x-ray radiation and the x-ray detector are stationary. In these computed tomography apparatuses an x-ray target is used that at least partially encloses the examination volume of the computed tomography apparatus in one plane. An x-ray focus from which the x-ray radiation emanates is generated on this target, the x-ray focus moving around the examination volume. These computed tomography apparatuses thus operate entirely without a mechanically moving x-ray tube. The x-ray target extends either completely around the examination volume or at least over an angle of more than 180°. In the same way the x-ray detector encloses the examination volume either completely or over an angle of at least 180° and is arranged such that the x-ray beam emanating from a moving x-ray focus passes through the examination volume onto respective, momentarily opposite detector elements of the stationary x-ray detector.

For example, U.S. Pat. No. 4,352,021 discloses a computed tomography apparatus of the fifth generation in which the x-ray target and the x-ray detector respectively surround the examination volume over an angle of approximately 210° For generation of the x-ray focus, an electron beam is generated with an electron gun and is directed over the x-ray target by suitable deflection. Due to numerous disadvantages, however, this technique (also known under the abbreviation EBCT (Electron Beam Computed Tomography)) has previously not found significant use in clinical application. A tilting of the examination plane in such systems is not possible. Like the accessibility of the patient for the operator, the available region for the horizontal positioning of the patient is severely limited. Such an x-ray computed tomography apparatus requires a very large examination room. Due to the long path of the electron beam, instabilities of the focus as well as a larger focus diameter occur, causing the spatial resolution to be impaired. The complex electron beam optics and long setup times lead to a lower reliability and lower patient throughput.

To avoid the problem associated with the long electron beam, U.S. Pat. Nos. 6,181,765 and 6,731,716 disclose x-ray computed tomography apparatuses of the fifth generation wherein an annular x-ray tube is used in which a number of thermal electron emitters are arranged distributed around the ring. Such thermal emitters, however, require a high electrical power in order to keep them at the required temperature during a scan. A comparable arrangement in which a field emission source is used as an electron source is known from United States Patent Application Publication No. 2002/0094064 A1. The individual regions of this cold electron source can be selectively addressed by an attached electrode structure in order to be able to emit electrons locally by means of the local electrical field. In these x-ray tubes the field emission current is controlled by the voltage applied at the electron source and not by the temperature, as in the thermal electron emitters. Cold electron sources are not yet able to generate the power/current densities required for many computed tomography apparatus applications with an acceptable lifespan. The electrical control of the many thousands of emitters arranged in an x-ray tube is additionally very costly.

U.S. Pat. No. 4,606,061 discloses a further embodiment of a computed tomography apparatus of the fifth generation in which an x-ray focus moving around the examination volume is generated on an x-ray target completely annularly surrounding the examination volume. An electron source ring that is coaxial with the x-ray target is likewise provided that is controlled by a laser beam directed with a laser scanning unit over its surface for electron emission. The laser scanning unit is arranged on the central ring axis of the electron source ring in order to be able to symmetrically scan this over an angle of 360°. Even this technique, however, does not avoid all problems associated with the EBCT technique. The scanning beam path must be shielded in such a system in order to avoid an unwanted interruption by the operator or other objects within the examination room. This also clearly limits the region available for a horizontal displacement of the patient as well as the accessibility of the patient for an operator.

SUMMARY OF THE INVENTION

An object of the present invention is to provide an x-ray computed tomography apparatus of the fifth generation in which access to the patient as well as the available region for a horizontal displacement of the patient table are less severely limited and more of the disadvantages of EBCT systems that were cited above are avoided.

This object is achieved in accordance with the invention by the x-ray computed tomography apparatus having a stationary x-ray detector that at least partially surrounds the examination volume in one plane and a stationary device for generation of x-ray radiation. The device for generation of x-ray radiation includes an x-ray source that extends annularly around the examination volume over an angle of at least 180° as well as one or more light scanning units with which an x-ray focus moving along the x-ray source can be generated on the x-ray target of the x-ray source by scanning of the x-ray source with a light beam, from which x-ray target an x-ray beam is directed through the examination volume onto respective, momentarily opposite detector elements of the stationary x-ray detector. The computed tomography apparatus has one or more light scanning units arranged and fashioned outside of a central ring axis of the x-ray source such that only an angle range <360° is respectively scanned with each light scanning unit without crossing the ring axis. For this purpose the one or more light scanning units are advantageously arranged and fashioned such that each light scanning unit scans the x-ray source respectively only over an angle of $\leq 270°$, in particular $\leq 210°$. Furthermore, the one or more light scanning units advantageously exhibit at least one interval with regard to the ring axis, this interval corresponding to the interval of a housing surrounding the x-ray source relative to the ring axis.

In one embodiment of the computed tomography apparatus according to the invention, the x-ray source has an arrangement composed of electron source and x-ray target situated opposite the electron source at a slight distance, the electron source and x-ray target extending annularly around the examination volume over the angle of at least 180°. An x-ray focus moving along the x-ray target is generated on the x-ray target by scanning of the electron source with the light beam of the light scanning units.

The arrangement composed of an electron source and an x-ray target can exhibit a design as is known, for example, from the already-cited U.S. Pat. No. 4,606,061. The electron source is formed of a material that releases electrons upon being struck by a light beam of sufficient intensity. The electrons are accelerated in the direction of the x-ray target by an electrical field in order to generate x-ray radiation in a known manner upon striking the x-ray target. For example, the electrons can be released from the electron source by visible or ultraviolet light through a photoelectric process, or with infrared light through a thermal process. In a preferred embodiment, cold electron emitters are used that can be activated by light.

The acceleration of the electrons in the direction of the x-ray target can be achieved by the application of a high electrical voltage between the x-ray target and the electron source, the electron source representing the cathode and the x-ray target representing the anode. In the inventive computed tomography apparatus the electron source and the x-ray target can be fashioned as one unit, or can be formed by a number of parts in an annular arrangement. Furthermore, optical deflection devices (such as, for example, a curved mirror) can be arranged in the region of the electron source in order to direct the light radiation of a light scanning unit (which light radiation is incident at various angles) perpendicularly onto the surface of the electron source.

In an alternative embodiment of the computed tomography apparatus, the x-ray radiation is directly generated by the incoming light beam. This requires the use of laser pulses of high intensity or pulse power that generate a hot plasma on the surface of the x-ray target upon impact on the x-ray target of the x-ray source, from which hot plasma the x-ray radiation emanates (plasma-generated x-ray radiation). For this purpose, the laser pulses should exhibit energy densities of >1014 W/cm2 in order to be able to generate x-ray radiation in the energy range (50 . . . 140 keV) required for medical diagnostics.

In contrast to the computed tomography apparatus of U.S. Pat. No. 4,606,061, in the computed tomography apparatus of the present patent application the one or more light scanning units are neither arranged on the ring axis of the x-ray source nor scan an angle of 360° (corresponding to a full rotation of the x-ray focus). Instead, the light scanning units are arranged and fashioned outside of this axis such that only a sub-segment of the whole angle range of 360° is scanned by each light scanning unit without crossing the ring axis. This enables an arrangement in which the displaceable part of the patient positioning table with the examination subject can be arbitrarily displaced in the horizontal direction without coming into contact with the light scanning units or their scanning radiation or, respectively, a housing surrounding these. The available region for a horizontal displacement is therewith distinctly expanded relative to the known systems of the prior art. Furthermore, the accessibility of a patient positioned on the patient positioning table is thereby improved for the operator.

Given use of only one light scanning unit, it scans a sub-segment that, although it must correspond to an angle range of $\geq 180$ for the generation of a computed tomography exposure, is distinctly smaller than 360° in order to not impair the displacement capability of the patient positioning table in the horizontal direction. In this case the annular x-ray source also dies not extend over an angle of 360°, but instead merely over the scanned angle range.

Given use of more than one light scanning unit, a sub-segment <180° can also be scanned by each individual light scanning unit as long as the total scanned sub-segments yield a contiguous angle range of $\geq 180°$ in order to be able to generate an x-ray focus moving on the x-ray target over this angle range.

In a further embodiment, two light scanning units are provided that generate an x-ray focus running over an angle of 360°. Each of the two light scanning units scans a different sub-segment of the x-ray target or of the electron source over an angle range of respectively 180°. Both the x-ray source and the x-ray detector are naturally fashioned as a full ring.

Lasers are advantageously used as light sources. The one or more laser scanning units thus can each include in a known manner, a pulsed laser as well as a suitable deflection device for the laser beam. This deflection device can, for example, be an x-y galvanometer scanner as it is known from optical projection systems. The deflection speeds (sweep) lie in the range of a few kilohertz. In an embodiment of the inventive computed tomography apparatus with a number of laser scanning units, these are alternately operated via a suitable control unit such that the laser pulses of the laser scanning units alternately strike the x-ray source or the x-ray target. The thermal load of the x-ray target and the laser is reduced in this manner.

DESCRIPTION OF THE DRAWINGS

FIG. 1 shows an example for the design of a computed tomography apparatus in a side view in accordance with the invention.

FIG. 2 shows an example for the scanning beam path of the laser scanning unit in a computed tomography apparatus according to the invention.

FIG. 5 is an example of a back view of the inventive computed tomography apparatus.

FIG. 6 is an example of the design of an inventive computed tomography apparatus with two laser scanning units.

DESCRIPTION OF THE PREFERRED EMBODIMENTS

Figure 3:
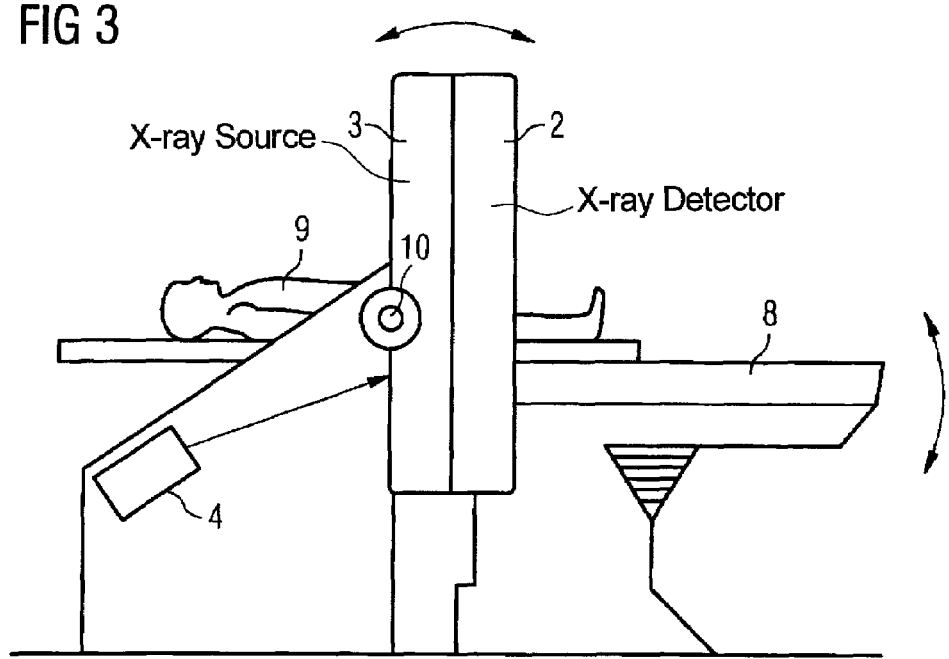
FIG. 3 shows an example for the design of the inventive computed tomography apparatus with a tilting of the acquisition plane.

FIG. 1 shows an example for the design of a computed tomography apparatus according to the present invention. The computed tomography apparatus has an image acquisition arrangement 1 as well as a displaceable patient positioning table 8 on which is borne a patient 9 is supported in the present example. The image acquisition arrangement 1 in the present example has two partial rings, of which one partial ring includes the x-ray detector 2 and a second partial ring includes the x-ray source 3 (in this example an arrangement composed of electron source and an x-ray target). Electrons are generated with a laser scanning device 4 via a scan along the partial ring-shaped electron source and said electrons are accelerated onto the x-ray target such that an x-ray focus moving on the partial ring-shaped x-ray target is generated. The limitations of the scanning regions of the laser scanning unit 4 are indicated by the laser beams 5 in FIG. 1. The two partial rings of the x-ray detector 2 and the x-ray source 3 are offset relative to one another such that an x-ray beam 6 emanating from the moving x-ray focus passes through the examination volume onto respective, momentarily opposite detector elements of the x-ray detector 2.

In the present example the laser scanning unit 4 exhibits a spacing or distance from the ring axis 12 of the partial ring of the x-ray source 3 that is greater than the separation of this partial ring relative to the ring axis 12, such that the patient positioning table 8 with the patient 9 can be displaced in the horizontal direction unhindered. For this purpose the separations can also be equal. Furthermore, the laser scanning unit 4 sweeps over only an angle of approximately 210°, such that the patient positioning table 8 with the patient 9 is also not limited in its movement by the scanning beam. This can be more clearly seen in FIG. 2, which shows the partial ring with the x-ray detector 2 and the partial ring offset relative to this with the arrangement made up of electron source and x-ray target from another perspective. In this representation the scan region of the scanning unit 4 is indicated by the laser beams 5. From this representation it is clear that the maximum diameter of the examination volume (80 cm in the present example) that is predetermined by the partial rings is also not limited by the scanning outside of the partial rings. By means of the scanning selected in this example over an angle of approximately 210°, an x-ray focus moving on the x-ray target over this angle range is generated from which an x-ray beam 6 emanates. The circumferential range of the x-ray beam of 210° is sufficient for a computed tomography data acquisition.

Two circumferential cooling tubes 7 via which the x-ray detector 2 a well as the x-ray source 3 are cooled during the operation are additionally shown in the example of FIG. 1. Air or water is suitable as a cooling medium, for example.

FIG. 3 shows a representation of such an x-ray computed tomography apparatus in which the image acquisition arrangement 1 can be tilted on a tilt axis 10 relative to the patient positioning table 8 with the patient 9 borne thereupon. This tilt capability is indicated by the two double arrows shown in the Figure. Slice images of the patient that are not situated perpendicular to the z-axis (examination axis) can be acquired via a tilting of the image acquisition arrangement 1. The tilting requires the mechanical connection between the laser scanning unit 4 and the two partial rings composed of the x-ray detector 2 and the arrangement with the electron source and the x-ray target. Alternatively, the patient positioning table 8 can also be tilted. The tilting can, for example, ensue at a tilt angle of +/− 15°.

Figure 4:
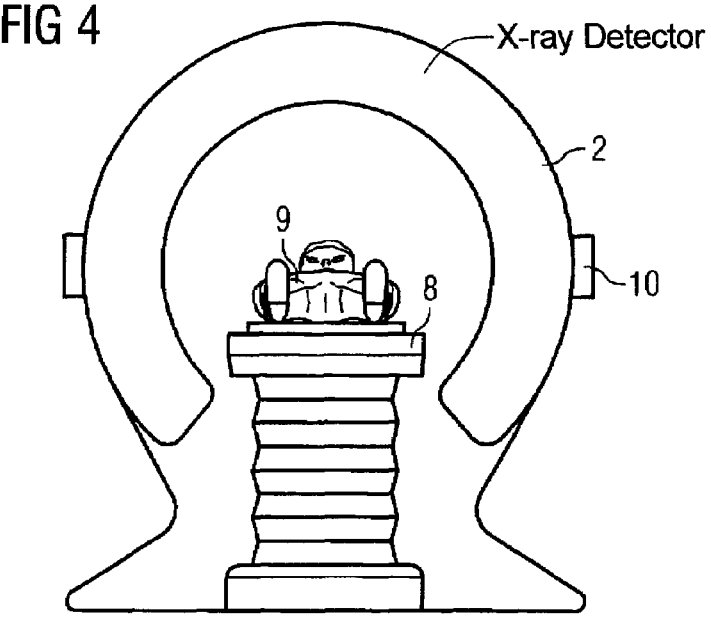
FIG. 4 is an example of front view of the inventive computed tomography apparatus.

FIG. 4 shows an example for a front view of the x-ray computed tomography apparatus. To be recognized in the Figure are the patient positioning table 8 with the patient 9 as well as the partial ring of the x-ray detector 2. The tilt axis 10 is likewise indicated.

FIG. 5 shows a rear view of such a computed tomography apparatus in which the partial ring with the arrangement made up of electron source and x-ray target, the laser scanning unit 4 as well as the uncovered part of the partial ring of the x-ray detector 2 can be seen.

Figure 7:
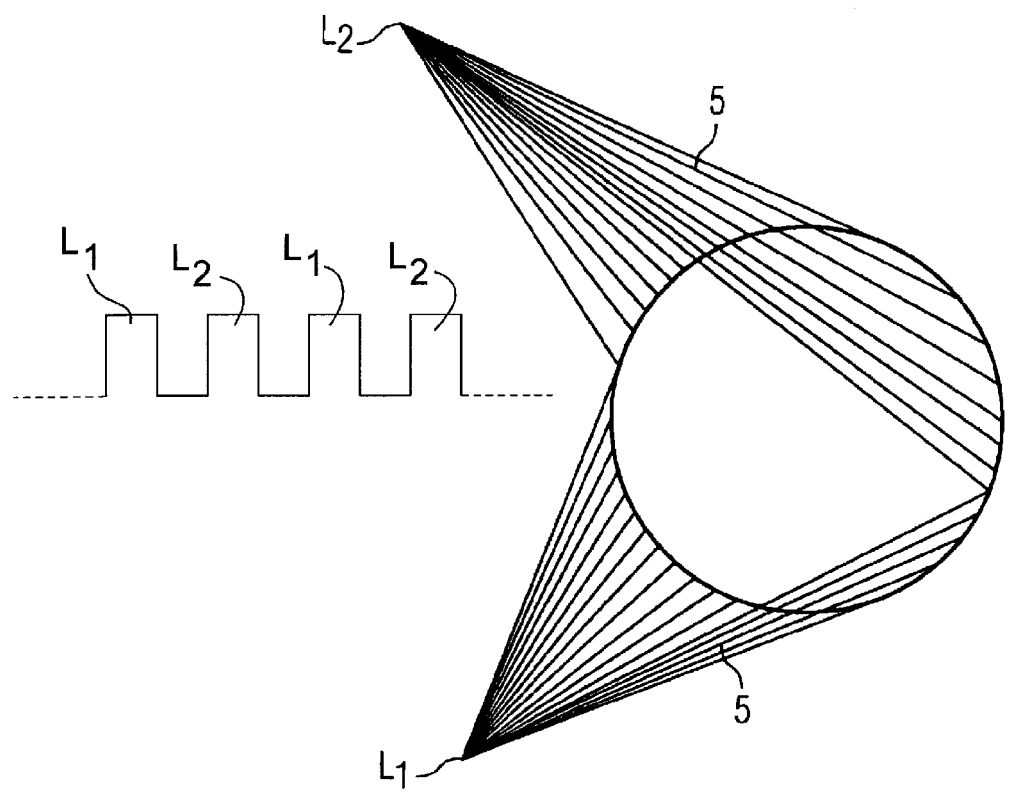
FIG. 7 is an example for the scanning beam path of both laser scanning units.

FIG. 6 shows a further exemplary embodiment of the present x-ray computed tomography apparatus. In this embodiment both the x-ray detector 2 and the arrangement made up of an electron source and an x-ray target (x-ray source 3) respectively form a complete ring, whereby both rings are arranged parallel to one another. The scanning of the electron source ensues via two laser scanning units 4 that respectively scan an angle of 180° and are arranged far enough outside of the ring axis 12 in order to not limit the horizontal movement space for the patient positioning table 8. FIG. 7 in turn exemplarily shows the scanning beam paths of both laser scanning units 4 with the lasers L1 and L2 using the laser beams 5. An x-ray focus running over an angle of 360° can thus be generated with this arrangement, from which x-ray focus a correspondingly running x-ray beam 6 emanates. Both the device for generation of the x-ray radiation and the x-ray detector 2 are thereby stationary, as before.

The pulsed lasers L1, L2 of the laser scanning units 4 are operated in alternation during the image acquisition in order to reduce the thermal load of both lasers as well as of the x-ray target. In FIG. 7 the pulse series of both lasers L1 and L2 are schematically indicated.

Figure 8:
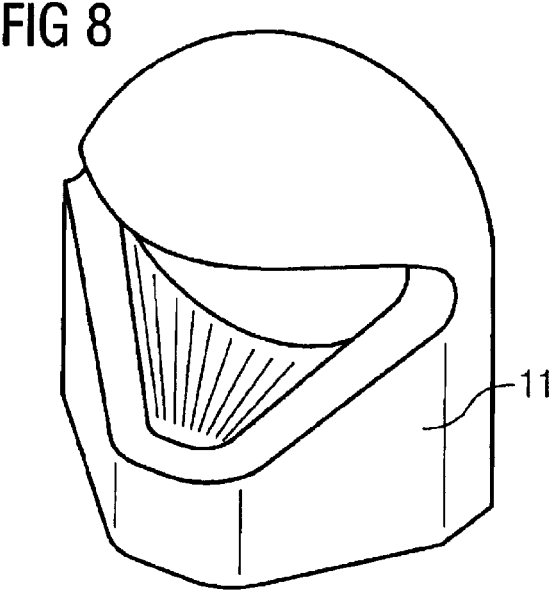
FIG. 8 is an example for a back view of the computed tomography apparatus of FIG. 6.

FIG. 8 shows an example for the form of the housing 11 given a computed tomography apparatus fashioned according to FIG. 6.

In a further embodiment, one or more shaping elements for influencing of one or more beam parameters of the generated x-ray beam 6 between the x-ray target and the detector elements of the x-ray detector 2 are arranged on a rotary frame that can be rotated around the ring axis 12 in sync with the movement of the x-ray focus. These shaping elements (in particular with the function of collimators) can both delimit the aperture angle of the x-ray beam 6 in the slice plane (X-Y plane) and/or in the Z-direction and be fashioned as filters that influence the intensity profile of the x-ray beam 6 or its spectral distribution. The shaping elements can also form a scattered-ray grid for the x-ray detector 2.

Furthermore, a device for reduction of a portion of positive ions can be arranged in the region of the electron source in order to increase the lifespan of the electron source. This device can be an electrode system that captures positive ions upon application of a direct or alternating voltage. The arrangement of this electrode system, for example an ICE or RICE electrode system, ensues such that the proportion of positive ions in the region of the electron source is reduced in order to prevent or at least to severely reduce the bombardment of the surface of the electron source by such ions. Moreover, the proportion of positive ions in the focuser region of the electron beam (i.e. In the region immediately before the x-ray target) should not be significantly reduced in order to be able to contribute to the neutralization of the repelling forces of the electrons of the electron beam and therewith to the good focusing capability of this electron beam. The electrode system is therefore preferably arranged closer to the electron source than to the x-ray target.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray computed tomography apparatus comprising:
   a stationary x-ray detector completely surrounding an examination volume in a first plane, and comprising a plurality of detector elements;
   a stationary device for generating x-ray radiation, comprising a single x-ray source extending annularly, relative to a ring axis, around said examination volume through an angle of 360° in a second plane, said first and second planes being perpendicular to said ring axis and defining a planar volume in which said examination volume is contained, and at least two light scanning units that each scan said x-ray source with a light beam to produce, in combination, an x-ray focus, moving along said x-ray source, on a target surface of said x-ray source, from which an x-ray beam emanates into and moves through said examination volume and successively strikes respective detector elements of said stationary x-ray detector that are momentarily opposite said x-ray focus; and
   said at least two light scanning units being disposed outside of said planar volume and each light scanning unit scanning only an angle range of less than 360°, without crossing said ring axis and, in combination, causing said x-ray focus to move through said angle of 360°.

2. An x-ray computed tomography apparatus as claimed in claim 1 wherein said x-ray source comprises an electron source and said electron target, forming said target surface, situated opposite said x-ray source, and wherein said x-ray focus moving along said target surface is generated on said electron target by scanning said electron source with said at least one light scanning unit.

3. An x-ray computed tomography apparatus as claimed in claim 1 wherein said x-ray source comprises a housing surround said x-ray source disposed at a distance from said ring axis, and wherein said at least one light scanning unit disposed at a distance from said ring axis substantially corresponding to said distance of said housing from said ring axis.

4. An x-ray computed tomography apparatus as claimed in claim 1 wherein said device for generating x-ray radiation and said x-ray detector are mounted in a tiltable unit that allows tilting of said device for generating x-ray radiation and said x-ray detector together at an angle relative to an examination axis.

5. An x-ray computed tomography apparatus as claimed in claim 1 wherein said at least one light scanning unit is a laser.

6. An x-ray computed tomography apparatus as claimed in claim 1 comprising at least two light scanning units, each comprising a pulsed laser, and wherein said x-ray computed tomography apparatus comprises a control unit for operating said at least two light scanning units to emit respective laser pulses alternating with each other, said respective laser pulses from said pulsed lasers striking said x-ray source in alternation.

* * * * *